| United States Patent [19] | [11] Patent Number: | 4,891,211 |
|---|---|---|
| Winston | [45] Date of Patent: | Jan. 2, 1990 |

[54] STABLE HYDROGEN PEROXIDE-RELEASING DENTIFICE

[75] Inventor: Anthony E. Winston, East Brunswick, N.J.

[73] Assignee: Church & Dwight Co., Inc., Princeton, N.J.

[21] Appl. No.: 212,913

[22] Filed: Jun. 29, 1988

[51] Int. Cl.$^4$ .......................... A61K 7/16; A61K 7/18; A61K 7/20
[52] U.S. Cl. ...................................... 424/52; 424/49; 424/53
[58] Field of Search ...................... 424/495, 352, 283

[56] References Cited

U.S. PATENT DOCUMENTS

| 3,886,265 | 5/1975 | Evers et al. | 424/49 |
| 4,582,701 | 4/1986 | Piechota | 424/52 |
| 4,647,451 | 3/1987 | Piechota | 424/52 |

*Primary Examiner*—Shep K. Rose
*Attorney, Agent, or Firm*—Bryan, Cave, McPheeters & McRoberts

[57] ABSTRACT

A stable, palatable and safe hydrogen peroxide-releasing toothpaste or gel dentifrice comprising sodium bicarbonate and sodium percarbonate in a polyethylene glycol base. Thickening agents, surfactants, flavoring agents, sweeteners, fluoridating agents, and other conventional adjuvants may also be included in the dentifrice formulation.

20 Claims, No Drawings

STABLE HYDROGEN PEROXIDE-RELEASING DENTIFICE

TECHNICAL FIELD

This invention relates to a stable, palatable sodium bicarbonate-containing hydrogen peroxide-releasing dentifrice in the form of an opaque toothpaste or a translucent (i.e., visually clear or Partially clear) gel.

BACKGROUND OF THE INVENTION

Periodontal disease afflicts over an estimated 90 percent of the world's population. Lassari, E.P., *Dental Biochemistry*, 191-3, (1976). Although this disease is not life threatening, it often results in serious discomfort and tooth loss. The basic cause of this disease is bacteriological in nature. Both topical and systemic bactericidal agents have been found effective in combating the disease. *Biological Basis of Periodontal Maintenance Therapy*, G.C. Armitage, Proxis Publishing Company, 1980, pp. 34-78.

Recently, it has been demonstrated that combinations of various salts and hydrogen peroxide solution, when properly applied as part of a treatment under the supervision of a dentist, are effective in controlling periodontitis. B.G. Rosling et al., Journal of Clinical Periodontology, Vol. 10 pp. 487-514, 1983. Sodium bicarbonate, a particularly convenient and palatable non-toxic salt, is believed to be effective in this treatment. Keyes P.H. et al., Quintessence International No. 1, January 1978, report 1590, pp. 51-56 and No. 2, February 1978, pp. 69-75.

The bacteria causing periodontal disease are anaerobic. Armitage, G.C., Biological Basis of Periodontal Maintenance Therapy, 1980. By providing high levels of oxygen, hydrogen peroxide is believed to be effective in killing these bacterial organisms. Hydrogen peroxide is the preferred oxidizing agent as it is readily available, proven effective and non-toxic.

In addition to treating periodontal disease, many individuals like to use baking soda and peroxide to clean their teeth. Several of the benefits cited by those using this combination include ability to remove stains, a clean feeling in the mouth, less mouth odor and healthy gums.

A mixture of an approximately 60 percent sodium bicarbonate paste with a 3 percent solution of hydrogen peroxide has been used to treat periodontal disease. This method requires the user, immediately before use, to prepare the mixture in the palm of the hand. The mixture is then applied along the gum line. Due to the foaming action of the hydrogen peroxide, and because the mixture is prepared on the palm of the hand, this procedure is messy.

To overcome the inconvenience of the above procedure, various dentifrices have been formulated which contain oxidizing aqents such as sodium perborate (Cella, et al., U.S. Pat. No. 3,885,028 and Molnar, U.S. Pat. No. 2,275,979), potassium chlorate, urea peroxide (Gordon, U.S. Pat. No. 4,522,805 and Schaeffer, U.S. Pat. No. 4,528,180) and magnesium peroxide. Balsam, M.S. et al, Cosmetics: Science and Technology, Volume 1, Second Edition, Wiley Interscience (1972) page 496.

Sodium perborate and potassium chlorate do not release significant levels of hydrogen peroxide in water. Kirk-Othmer Encyclopedia of Chemical Technology, Third Edition, Volume 17, pages 1-22; Kern, D.M., J. Am. Chem. Soc. 77:5458, 1955. Although sodium perborate has been classified category 1 (Federal Register, Oct. 7, 1982) for temporary use as an oral wound cleaner, it is of questionable safety for frequent topical use on the mucous membranes of the mouth and throat because it contains boron which can undergo systemic absorption. (Federal Register Vol. 44 No. 214 page 63282, Fri., Nov. 2, 1979, Proposed Rules). Sodium perborate also has an undesirably low solubility in water of about 2.5%. This low solubility limits the concentration of oxidizing agent. Magnesium peroxide, an essentially insoluble salt in water, is similarly undesirable. Handbook of Chemistry and Physics, 59th Ed., 1978-79.

Various peroxide releasing dentifrice formulations utilize urea peroxide as the oxidizing agent. See U.S. Pat. No. 4,522,805. However, sodium bicarbonate/urea peroxide dentifrices are not stable, presumably because hydrogen peroxide solutions are not stable at alkaline pH (see "Hydrogen Peroxide," Schumb, Satterfield & Wentworth, American Chemical Society Monograph No. 128 (1955), pp. 526-530). As a result, dentifrice preparations have been proposed in which the urea peroxide and sodium bicarbonate components are placed in separate compartments of a container (see Schaeffer, U.S. Pat. No. 4,528,180, column 2, lines 4-9,). However, a uniform ratio of peroxide and bicarbonate in the formulation disclosed in Schaeffer is not assured. Further, where the two incompatible pastes are dispensed through a single nozzle, there is a possibility of reaction between the two pastes at the point at which they come in contact inside the tube.

Alkali and alkaline earth metal percarbonates, e.g., ammonium percarbonate, were also described as peroxide releasing agents for dentifrices more than 80 years ago. (Gane, U.S. Pat. No. 802,099 granted Oct. 17, 1905.) The percarbonates have not previously been used in dentifrice formulations, however, because of their high pH in solution which could cause severe gum irritation. One safe, palatable and convenient formulation containing sodium bicarbonate and sodium percarbonate in the form of a stable tooth powder has recently been described in U.S. Application Ser. No. 017,143, filed Feb. 20, 1987 and assigned to the owner of the present invention. However, no stable toothpaste or gel dentifrices are currently known, which combine sodium bicarbonate with sodium percarbonate.

It is accordingly among the objects of the present invention to provide a stable, peroxide releasing toothpaste and dentifrice gel. It is a further object of the invention to provide such a formulation which is useful in the treatment of periodontal disease and which minimizes dental caries, in a safe, more convenient and palatable form than embodied in any known prior art formulation.

SUMMARY OF THE INVENTION

In accordance with the present invention, a toothpaste or gel dentifrice is provided, comprising a mixture of up to about 70% sodium bicarbonate with about 1 to 10% sodium percarbonate, in a carrier which is substantially free of glycerin and which comprises about 20 to 75% of a polyethylene glycol humectant. Dentifrices prepared in accordance therewith provide a pre-mixed, stable combination of sodium bicarbonate and peroxide-releasing agent in a palatable and convenient form.

It has been found that toothpastes or gels containing the noted ingredients, either with or without other dentifrice adjuvants such as fluorides (e.g., sodium fluoride), sweeteners (e.g., saccharin), flavorants, etc., are quite palatable and surprisingly stable with regard to loss of oxygen, as compared with dentifrices prepared from other bicarbonate/hydrogen peroxide-releasing formulations e.g., those containing urea peroxide (see for example, Controls D-F in Tables III and V below).

Moreover, the present formulation, in which the carrier principally comprises a polyethylene glycol humectant, is surprisingly more stable than analogous dentifrices containing other conventional vehicles such as glycerin or propylene glycol (see Controls A-C in Table II below). A dentifrice incorporating even as little as 10% glycerin has been found to exhibit unacceptable stability characteristics (Control C).

On the other hand, the formulation of the invention surprisingly exhibits satisfactory stability characteristics, even in the presence of up to about 3% water (see Example 3 in Table II below). When, as noted below, an anhydrous hydratable salt such as sodium acetate is additionally incorporated in the dentifrice, it exhibits increased stability notwithstanding the presence of water (compare Examples 3 and 5, and Control G, in Table VI below). It is believed that the hydratable salt acts to scavenge any water present, thereby minimizing percarbonate dissolution and hydrogen peroxide release and thus stabilizing the oxygen content of the dentifrice.

Furthermore, the dentifrice formulation hereof incorporates the relatively inexpensive hydrogen peroxide-releasing agent, sodium percarbonate, in a quite safe and palatable form. As indicated above, sodium percarbonate cannot normally be utilized in the oral cavity because it has an excessively high pH in solution which could cause severe irritation of the gums. The presence of sodium bicarbonate in admixture therewith serves to reduce the pH and provide a safe and palatable dentifrice.

In addition to the preceding advantages, the product of the invention is more convenient to use, less messy and has greater esthetic appeal than previous formulas which the user must mix immediately before use and which might contain varying proportions of the active ingredients.

DETAILED DESCRIPTION

Sodium bicarbonate is incorporated in the dentifrice of the present invention in an amount of about 10 to 65%, preferably within the range of about 30 to 60%, by weight. For toothpaste formulations, preferably at least 30% of the sodium bicarbonate abrasive has particle sizes less than about 25 microns, and the median particle size is desirably less than 44 microns (Grade 3DF). Use of bicarbonate abrasive particles of this size range imparts an acceptable level of abrasivity and smooth consistency to the product. Coarser grades of baking soda could be used if desired for particular applications or when a more granular texture is desired. Coarser grades of bicarbonate are particularly desirable when clear or partially clear gels are desired (see copending application Serial No. 197,218 filed May 23, 1988, entitled "Dentifrice Gels Containing Sodium Bicarbonate" [11785/40003]).

The hydrogen peroxide-releasing agent, sodium percarbonate, is present in the dentifrice in an amount of about 1 to 10%, preferably within the range of about 2-6%, by weight.

The mixture of the bicarbonate and percarbonate is incorporated in a carrier which principally comprises a polyethylene glycol (PEG) humectant suitably incorporated in an amount of about 20 to 75% by weight of the dentifrice. The preferred polyethylene glycol humectants are those having molecular weights between about 200 and 600, e.g., polyethylene glycols sold as Carbowax 200, 300, 400 or 600.

The dentifrice of the invention preferably contains other conventional adjuvants in addition to sodium bicarbonate, sodium percarbonate and polyethylene glycol. Such ingredients may include thickeners, sweeteners, flavors, fluoridating agents, surfactants, additional abrasives, or other additives known in the art.

Thickeners which are useful for thickening the pastes or gels include the solid polyethylene glycols having molecular weights above about 900, e.g., those sold as Carbowax 900, 1000, 1450, 3350, 4600 or 8000, and the inorganic amorphous silicas, desirably the hydrogels (such as Sylodent 15 or Sylodent 2 from W.R. Grace and Co.), or the pyrogenic or fumed silicas (such as Aerosil 200 from Degussa, or Cabosil from Cabot).

In general, it has been found that most other conventional organic gelling agents such as sodium CMC are not effective in thickening the dentifrice of the present invention because they require the presence of water to induce swelling. Organic thickeners which are soluble in polyethylene glycol and which do not require water to increase their viscosities in solution may be effective to impart a desirable viscosity and texture to the dentifrice hereof.

The inorganic amorphous silica thickeners may be incorporated in the dentifrice of the invention in amounts of up to about 10%, preferably about 1.0 to 3.0% thereof. On the other hand, the organic thickeners may comprise up to about 5%, preferably about 0.5 to 2.0%, of the composition.

Suitable sweeteners may also be included in the dentifrice of the invention. Such sweeteners include sucrose, lactose, maltose, sorbitol, saccharin, sodium or calcium cyclamate, aspartame or other sweeteners known to those skilled in the art. The sweetener is desirably present within the range of from about 0.1 to 5.0%.

Flavoring agents useful in the dentifrice of the present invention include the flavoring oils, for example, oils of peppermint, spearmint, menthol, wintergreen, clove, sassafras, cinnamon, lemon, orange, licorice, sage, marjoram or eucalyptus, as well as sodium methyl salicylate. The flavoring agent may be present in the dentifrice in an amount of about 0.2 to 2.0% by weight of the dentifrice, preferably within the range of about 0.5 to 1.0%.

The dentifrice may additionally contain a fluoridating agent for the prevention of dental caries. Fluoridating agents suitable for use herein include the sodium, potassium, ammonium, lithium, and amine fluorides, stannous fluoride or chlorofluoride, potassium stannous fluoride ($Sn_nF_2KF$), and complex fluoride salts such as sodium fluozirconate and sodium, potassium, ammonium or lithium monofluorophosphate. The fluoridating agent is desirably present in an amount of about 0 to 3.0% by weight of the dentifrice. Preferably, the dentifrice contains from about 1000 to 2000 ppm fluoride ion, either in the form of a fluoride or monofluorophosphate salt. This level may be provided by 0.22% to 0.44% sodium fluoride or 0.76% to 1.52% sodium monofluorophosphate.

Suitable surfactants include water soluble anionic surfactants such as the sulfates of long chain ($C_8$–$C_{18}$) alcohols, e.g., sodium lauryl sulfate or sodium tridecylsulfate; the sulfates or sulfonates of monoglycerides of fatty acids, e.g., sodium lauroyl glyceryl sulfate or sodium coconut monoglyceride sulfonate; the sulfonates of succinic esters, e.g., sodium dioctyl sulfosuccinate; the alkyl sulfoacetates such as sodium lauroyl sulfoacetate or sodium coconut sulfoacetate; the salts of sulfoacetic acid modified by aminoethyl long chain fatty acid esters such as sodium sulfocolaurate; the amides formed from higher fatty acids with short chain aliphatic amino acids such as sodium lauroyl sarcosinate or sodium methyl lauroyl tauride; and soaps such as the sodium, potassium or triethanolamine salts of fatty acids. Similarly, nonionic surfactants may be used such as the ethoxylated sugar esters of the higher fatty acids, for example, ethoxylated sorbitan monostearate and ethoxylated glycerol monostearate. Also, amphoteric surfactants such as the mono or dicarboxylated imidazoline derivatives of fatty acids, e.g., sodium lauryl dicarboxy imidazoline or sodium coconut dicarboxy imidazoline may be used. Cationic surfactants may also be used in the gel. Surfactants may be selected which additionally impart significant antibacterial action to the gel. Examples of such surfactants include benzyl dimethyl stearyl ammonium chloride and cetylpyridinium chloride.

The surfactant is incorporated in the dentifrice in an amount of about 0 to 5%, preferably within the range of about 0.2 to 2.0% of the dentifrice.

The dentifrice may also contain from about 0 to 40% by weight of an additional abrasive material or materials. Abrasive materials suitable as additional abrasives in the dentifrices of the present invention are well known in the art and include calcium carbonate, e.g., chalk; dicalcium phosphate dihydrate, anhydrous dicalcium phosphate, tricalcium phosphate, calcium pyrophosphate, sodium meta-phosphate; amorphous silica; alumina; titanium dioxide; zirconium silicate; and the like.

It is particularly desirable to include a secondary abrasive in gel formulations, since they contain relatively small proportions (usually about 10 to 40%) of the mild bicarbonate abrasive. In such instances, secondary abrasives of the type normally utilized in translucent dentifrice gels are incorporated in the gel in amounts of up to about 20%, preferably about 5 to 15% thereof. Polishing agents so useful include alkali metal phosphates and complex aluminosilicates such as described in U.S. Pat. Nos. 3,927,200; 3,906,090; 3,911,102; and 4,036,949; and, preferably, amorphous silica such as the hydrous silica gels (commercially available, for example, as Sylodent 700 and 756). One of the advantages of the hydrous silica gels is that they allow significant flexibility in adjusting the abrasivity of the formulation by varying the type or level of the hydrous silica gel used, as discussed in the aforesaid patent application on Dentifrice Gels Containing Sodium Bicarbonate. Dentifrices incorporating the noted proportions of these secondary abrasives retain the optical clarity (translucency) of gels.

As noted hereinabove, in order to preserve the stability of the dentifrice, it is preferred to add an anhydrous hydratable salt to the formulation. Examples of such anhydrous hydratable salts include sodium acetate, anhydrous mono-, di-, or trisodium phosphate, sodium carbonate, calcium sulfate and magnesium chloride. The hydratable salt is included in the dentifrice in an amount of about 0 to 10%, preferably about 1 to 4% thereof. It is desirable to include such a hydratable salt in the formulation even when water is not purposely added. The hydratable salt serves to scavenge any incidental moisture introduced. In a preferred form, the dentifrice of the present invention comprises:

| Ingredient | Percentage by Weight |
|---|---|
| Sodium Bicarbonate | 20 to 65% in toothpaste, 10 to 40% in gel |
| Sodium Percarbonate | 1 to 10% in toothpaste, 1 to 6% in gel |
| Secondary abrasive | Up to 40% in toothpaste, up to 20% in gel |
| Polyethylene Glycol | 20 to 75% in toothpaste, 20 to 75% in gel |
| Organic Thickener | up to 5%, preferably from 0.5 to 2.0% |
| Inorganic thickener | up to 10.0%, preferably from 1.0 to 3.0% |
| Surfactant | up to 5.0%, preferably from 0.2 to 2.0% |
| Flavoring agent | up to 2.0%, preferably from 0.5 to 1.0% |
| Sweetener | up to 5.0%, preferably from 0.2 to 1.5% |
| Anhydrous hydratable salt | up to 10%, preferably from 1.0 to 4.0% |
| Fluoridating agent | up to 3.0%, preferably to provide between 1000–2000 ppm fluoride ion |

The following Examples illustrate particularly preferred embodiments of the dentifrice of the invention. Unless otherwise noted, all parts and percentages specified above or given in the following examples are specified by weight of the complete dentifrice.

EXAMPLES 1-3

Comparison of Toothpaste Formulations Containing Different Humectants

Samples of the formulation of the invention, containing polyethylene glycols as the humectant, were prepared as Examples 1-3. Control preparations (Controls A–C) were also prepared, incorporating the following humectants as carriers thereof:
Control A-Propylene glycol;
Control B-Glycerin;
C-Polyethylene glycol/glycerin
The test preparations had the following compositions:

TABLE I

| | TOOTHPASTE FORMULATIONS | | | | | |
|---|---|---|---|---|---|---|
| | Example 1 | Example 2 | Example 3 | Control A | Control B | Control C |
| Polyethylene glycol 400 MW[1] | 31.05 | 32.45 | 30.45 | — | — | 21.15 |
| Polyethylene glycol 8000 MW[2] | 0.9 | 0.9 | 0.9 | 0.9 | 0.9 | 0.9 |
| Propylene glycol | — | — | — | 29.45 | — | — |
| Glycerol | — | — | — | — | 32.45 | 10.0 |
| Water | — | — | 2.0 | — | — | — |
| Sodium bicarbonate | 56.0 | 56.0 | 56.0 | 58.0 | 56.0 | 56.0 |
| Sodium percarbonate | 6.0 | 6.0 | 6.0 | 6.0 | 6.0 | 6.0 |
| Aerosil 200 (Degussa) | 2.0 | 3.0 | 1.0 | 2.0 | 1.0 | 2.0 |
| Sodium lauroyl | | | | | | |

TABLE I-continued

| | TOOTHPASTE FORMULATIONS | | | | | |
|---|---|---|---|---|---|---|
| | Example 1 | Example 2 | Example 3 | Control A | Control B | Control C |
| sarcosinate | — | — | — | — | — | 0.3 |
| Flavor | 0.75 | 0.75 | 0.75 | 0.75 | 0.75 | 0.75 |
| Saccharin | 0.9 | 0.9 | 0.9 | 0.9 | 0.9 | 0.9 |
| Sodium acetate | 2.4 | 0 | 2.0 | 2.0 | 2.0 | 2.0 |
| | 100.0 | 100.0 | 100.0 | 100.0 | 100.0 | 100.0 |

[1] Carbowax 400
[2] Carbowax 8000

The level of active hydrogen peroxide retained by each of the above formulations under simulated storage conditions was determined as follows:

About 1g of product was accurately weighed and transferred with the aid of water to a 250 ml iodine flask. Glacial acetic acid (5ml) was added and the solution mixed. Potassium iodide (2g) and one drop of ammonium molybdate solution were added and the solution was stored in the dark for 10 minutes. The liberated iodine was titrated with 0.1N sodium thiosulfate, and starch solution was added as an indicator as the endpoint was approached.

$$\% \ H_2O_2 = \frac{\text{mls (thiosulfate)} \times 0.1N \times 34 \times 100}{1000 \times 2 \times \text{wt (product)}}$$

The following stability data were obtained:

TABLE II

| | % of Active Hydrogen Peroxide | | | | | |
|---|---|---|---|---|---|---|
| | Ex. 1 | Ex. 2 | Ex. 3 | Control A | Control B | Control C |
| Initial % | 1.48 | 1.47 | 1.28 | 1.56 | 1.39 | 1.70 |
| 1 week at 40° C. | 1.46 | 1.43 | 1.36 | 1.38 | 0.23* | — |
| 3 weeks at 40° C. | — | — | — | — | — | 0.11 |
| 6 weeks at 40° C. | 1.52 | 1.46 | 1.22 | 1.10 | — | — |
| 4 weeks at Room Temp. | — | — | — | — | — | 1.63 |
| 6 weeks at Room Temp. | 1.41 | 1.43 | 1.46 | 1.34 | —* | — |

*Sufficient pressure built up that the bottom of the sealed sample tubes blew open.

The above data demonstrate that dentifrice formulas according to the invention (Examples 1-3) are remarkably stable with regard to the loss of oxygen over time, as compared with formulations containing other humectants, i.e., propylene glycol (Control A), glycerin (Control B), and combinations of PEG and glycerin (Control C).

EXAMPLE 4

Comparison of Toothpastes Containing Sodium Percarbonate and Urea Peroxide

The following further formulations were prepared:

TABLE III

| | Toothpaste Formulations | |
|---|---|---|
| | Example 4 | Control D |
| Polyethylene glycol (400 MW) | 31.15 | 31.15 |
| Polyethylene glycol (8000 MW) | 0.9 | 0.9 |
| Sodium bicarbonate | 56.0 | 56.0 |
| Urea Peroxide | — | 6.0 |
| Sodium Percarbonate | 6.0 | — |
| Aerosil 200 (Degussa) | 2.0 | 2.0 |
| Sodium Lauroyl Sarcosinate | 0.3 | 0.3 |
| Flavor | 0.75 | 0.75 |
| Saccharin | 0.9 | 0.9 |

TABLE III-continued

| | Toothpaste Formulations | |
|---|---|---|
| | Example 4 | Control D |
| Sodium Acetate | 2.0 | 2.0 |

The hydrogen peroxide contents of the respective formulations were determined in the same manner as described in connection with Examples 1-3:

TABLE IV

| | % of Active Hydrogen Peroxide | |
|---|---|---|
| | Example 4 | Control D |
| Initial % | 1.56% | 2.19% |
| 1 Day at Room Temp | — | End Seam of Sample blown out |
| 4 weeks at Room Temp | 1.56 | — |
| 3 weeks at 40° C. | 1.51 | — |

The tube containing Control D burst open after one day's storage at room temperature. In contrast, the dentifrice with the same formulation, except that the urea peroxide was replaced with sodium percarbonate (Example 4) was stable for at least four weeks at room temperature, and for three weeks at 40° C.

Comparison of Further Dentifrices Containing Urea Peroxide

Tests were run to determine the stability of toothpastes prepared according to Gordon, U.S. Pat. No. 4,522,805 (Controls E and F), containing urea peroxide as the hydrogen peroxide-releasing agent:

TABLE V

| | Toothpaste Formulations | |
|---|---|---|
| | Control E | Control F |
| Sodium Bicarbonate[1] | 15.0 | 25.0 |
| Calcium Carbonate | 8.0 | 15.0 |
| Urea Peroxide | 8.5 | 10.0 |
| Acidulated Sodium Fluoride[2] | 0.5 | 0.75 |
| Paste Carrier[3] | 68.0 | 49.25 |

[1] The mean particle size of the sodium bicarbonate crystals used was between 74 and 149 microns.
[2] The acidulated sodium fluoride consisted of a 1.8% sodium fluoride in water solution.
[3] The paste carrier contained, as a % of the finished formula:

| | | |
|---|---|---|
| Sorbitol | 20.2 | 14.6 |
| Sodium Lauryl Sulfate | 1.7 | 1.2 |
| Glycerol | 11.0 | 8.0 |
| Water | 32.4 | 23.5 |
| CMC | 0.9 | 0.65 |
| Flavor | 1.0 | 0.7 |
| Sweetener (Saccharin) | 0.2 | 0.2 |
| Preservative (Sodium Benzoate) | 0.6 | 0.4 |
| | 100.0 | 100.0 |

Control dentifrices E and F were filled into sealed toothpaste tubes. Tubes of each product were aged at room temperature and at 40° C. All the tubes burst within 24 hours, releasing their contents. The preceding results clearly show the instability of urea peroxide/bicarbonate dentifrices.

EXAMPLE 5

Comparison of Toothpastes Containing Varying Amounts of Water

Examples of the hydrogen-peroxide releasing dentifrice formulations of the invention containing water (Ex's. 3 and 5) were compared with a control containing 5% $H_2O$ (Control G). The respective compositions and relative stabilities, compared in the same manner as described in connection with Examples 1–3, were as follows:

TABLE VI

|  | Toothpaste Formulations | | |
|---|---|---|---|
|  | Example 3 | Example 5 | Control G |
| Polyethylene glycol (400 MW) | 30.45 | 32.65 | 29.65 |
| Polyethylene glycol (8000 MW) | 0.9 | 0.9 | 0.9 |
| Glycerin | — | — | — |
| Water | 2.0 | 2.0 | 5.0 |
| Sodium Bicarbonate | 56.0 | 56.0 | 56.0 |
| Sodium Percarbonate | 6.0 | 6.0 | 6.0 |
| Aerosil 200 | 1.0 | 0.5 | 0.5 |
| Sodium Lauroyl Sarcosinate | — | 0.3 | 0.3 |
| Flavor | 0.75 | 0.75 | 0.75 |
| Saccharin | 0.9 | 0.9 | 0.9 |
| Sodium Acetate | 2.0 | — | — |

TABLE VII

|  | % of Active Hydrogen Peroxide | | |
|---|---|---|---|
| Initial % | 1.28 | 1.73 | 1.63 |
| 1 week at 40° C. | 1.36 | — | — |
| 4 weeks at Room Temp. | — | 1.72 | 1.70 |
| 3 weeks at 40° C. | — | 1.24 | 0.69 |
| 6 weeks at 40° C. | 1.22 | | |
| 6 weeks at Room Temp. | 1.46 | | |

The preceding data demonstrate that formulations of the present invention containing up to 2% water (Ex's. 3 and 5) are more stable than formulas containing 5% water (Control G) after 3 weeks storage at 40° C. Further, the data demonstrate that the formula containing an anhydrous hydratable salt (Ex. 3) is significantly more stable than Example 5 which contained 2% water but no anhydrous hydratable salt additive (Ex. 5).

EXAMPLES 6 and 7

Formulations Containing Polyvethylene Glycol Humectants with Varying Molecular Weights Examples of hydrogen peroxide-releasing dentifrices containing polyethylene glycols of different molecular weights were prepared and their stabilities determined in the manner described in connection with the preceding examples:

TABLE VIII

|  | Toothpaste Formulations | |
|---|---|---|
|  | Example 6 | Example 7 |
| Polyethylene Glycol (300 MW) | 31.55 | — |
| Polyethylene Glycol (600 MW) | — | 31.15 |
| Polyethylene Glycol 8000 MW | 0.5 | 0.9 |
| Sodium bicarbonate | 56.0 | 56.0 |
| Sodium Percarbonate | 6.0 | 6.0 |
| Aerosil 200 | 2.0 | 2.0 |
| Sodium Lauroyl Sarcosinate | 0.3 | 0.3 |
| Flavor | 0.75 | 0.75 |
| Saccharin | 0.9 | 0.9 |
| Sodium Acetate | 2.0 | 2.0 |

TABLE IX

|  | % of Active Hydrogen Peroxide | |
|---|---|---|
| Initial % | 1.75% | 1.78% |
| 4 weeks at Room Temp. | 1.80% | 1.64% |
| 3 weeks at 40° C. | 1.61% | 1.59% |

The data demonstrate that dentifrices of the present invention in liquid PEG humectant carriers of varying molecular weights (Ex. 6, MW=300; Ex's 1–5, MW=400; and Ex. 7 MW=600) are all stable for long periods, both at room temperature and 40°.

EXAMPLES 8 and 9

Gel Formulations of the Invention

Gels having the following compositions were prepared:

|  | Gel Formulations | |
|---|---|---|
|  | Example 8 | Example 9 |
| Polyethylene glycol 400 MW[1] | 74.0 | 64.4 |
| Polyethylene glycol 8000 MW[2] | 4.0 | 3.9 |
| Sodium bicarbonate[3] | 15.0 | 21.4 |
| Sodium percarbonate | 2.0 | 2.9 |
| Aerosil 200 (Degussa) | 2.2 | 4.7 |
| Sodium lauryl sulfate | 0.2 | 0.2 |
| Flavor | 0.3 | 0.3 |
| Saccharin | 0.3 | 0.3 |
| Sodium acetate | 2.0 | 1.9 |
|  | 100.0 | 100.0 |

[1]Carbowax 400
[2]Carbowax 8000
[3]Sodium bicarbonate Grade 5, median particle size 149–210 u These formulations were somewhat granular, stable (Example 8–5 days aging at 40° C; Example 9—overnight aging at 40° C) gels (having clarity ratings of about 3 on the dentifrice gel clarity rating scale described in the aforesaid copending patent application).

The preceding disclosure is intended as illustrative only. The scope of the invention should be construed in accordance with the following claims:

1. A hydrogen-peroxide releasing dentifrice, comprising a toothpaste or gel containing a mixture of 10 to 70% sodium bicarbonate with from 1 to 10% sodium percarbonate, in a carrier which consists essentially of a polyethylene glycol humectant in an amount of from 20 to 75% of the dentifrice, said dentifrice being substantially free of glycerin and containing less than 3% water.

2. The dentifrice of claim 1, wherein the sodium bicarbonate is incorporated in an amount of from 10 to 65% by weight of the dentifrice.

3. The dentifrice of claim 2, wherein at least 30% of the sodium bicarbonate has particle sizes less than 25 microns.

4. The dentifrice of claim 1, wherein the sodium percarbonate is incorporated in an amount of from 2 to 10% by weight of the dentifrice.

5. The dentifrice of claim 1, wherein the polyethylene glycol carrier is a polyethylene glycol having a molecular weight of from 300 to 600.

6. The dentifrice of claim 1, further comprising from 1 to 10% by weight of an anhydrous hydratable salt effective to scavenge any incidental moisture.

7. The dentifrice of claim 1 wherein the anhydrous hydratable salt is sodium acetate, an anhydrous sodium phosphate, sodium carbonate, calcium sulfate or magnesium chloride.

8. The dentifrice of claim 1, further comprising from 1 to 3% by weight of an inorganic silica thickener.

9. The dentifrice of claim 1, further comprising from 0.2 to 5% polyethylene glycol thickener of molecular weight above 900.

10. The dentifrice of claim 1, further comprising from 0.1 to 3.0% by weight of a fluoridating agent.

11. The dentifrice of claim 1, further comprising from 0.2 to 2.0% of a surfactant.

12. The dentifrice of claim 1, further comprising from 0.2 to 2.0% by weight of a flavoring agent.

13. The dentifrice of claim 1, further comprising from 0.1 to 5.0% by weight of a sweetener.

14. The dentifrice of claim 1, further comprising a secondary abrasive selected from the group consisting of hydrous silica gels, alkali metal phosphates and complex aluminosilicates.

15. A hydrogen peroxide-releasing dentifrice which is substantially free of glycerin, which contains no more than 3% water, and which comprises:

| | |
|---|---|
| sodium bicarbonate | 10 to 65% |
| sodium percarbonate | 1 to 10% |
| secondary abrasive (a hydrous silica gel, alkali metal phosphate or complex aluminosilicate) | 0 to 40% |
| polyethylene glycol | 20 to 75% |
| organic thickener | 0.5 to 2.0% |
| inorganic thickener | 1.0 to 3.0% |
| surfactant | 0.2 to 2.0% |
| flavoring agent | 0.5 to 1.0% |
| sweetener | 0.2 to 1.5% |
| anhydrous hydratable salt effective to scavenge any incidental moisture (sodium acetate, an anhydrous sodium phosphate, sodium carbonate, calcium sulfate or magnesium chloride) | 1 to 4% |

16. The hydrogen peroxide-releasing dentifrice of claim 15, incorporating from 5 to 40% of the secondary abrasive.

17. The hydrogen peroxide-releasing dentifrice of claim 15, further comprising from 1000–2000 ppm fluoride ion.

18. The hydrogen peroxide-releasing dentifrice of claim 15, in form of a toothpaste containing:

| | |
|---|---|
| sodium bicarbonate | 20 to 65% |
| sodium percarbonate | 1 to 10% |
| secondary abrasive (a hydrous silica gel, alkali metal phosphate or complex aluminosilicate) | up to 40% |

19. The hydrogen peroxide-releasing dentifrice of claim 15, in the form of a gel comprising:

| | |
|---|---|
| sodium bicarbonate | 10 to 40% |
| sodium percarbonate | 1 to 6% |
| secondary abrasive (a hydrous silica gel, alkali metal phosphate or complex aluminosilicate) | up to 40% |

20. The hydrogen peroxide-releasing dentifrice of claim 15, further containing a fluoridating agent in an amount sufficient to provide between 1000–2000 ppm fluoride ion.

* * * * *

UNITED STATES PATENT AND TRADEMARK OFFICE
CERTIFICATE OF CORRECTION

PATENT NO. : 4,891,211

DATED : January 2, 1990

INVENTOR(S) : Anthony E. Winston et al.

It is certified that error appears in the above—identified patent and that said Letters Patent is hereby corrected as shown below:

Column 1: Title:      Change "DENTIFICE" to --DENTIFRICE--.
Column 1, line 3:     Change "DENTIFICE" to --DENTIFRICE--.
Column 1, line 9:     Change "Partially" to --partially--.
Column 1, line 30:    Change "al,," to --al.,--.
Column 1, line 57:    Change "aqents" to --agents--.
Column 6, line 18:    "In a preferred..." should start a new paragraph.
Column 6, line 53:    Before "C-Polyethylene" insert --control--.
Column 9, line 53:    Change "Polyvethylene" to --Polyethylene--.
Column 10, line 24:   After "40°" insert --C--.
Column 11, line 11:   Change "claim 1" to --claim 6--.
ABSTRACT, line 2:     Change "dentrifrice" to --dentifrice--.

Signed and Sealed this

Nineteenth Day of November, 1991

Attest:

HARRY F. MANBECK, JR.

Attesting Officer

Commissioner of Patents and Trademarks